(12) United States Patent
Ahmad et al.

(10) Patent No.: US 7,390,502 B2
(45) Date of Patent: Jun. 24, 2008

(54) SN-38 LIPID COMPLEXES AND THEIR METHODS OF USE

(75) Inventors: Imran Ahmad, Wadsworth, IL (US); Jia-Ai Zhang, Vernon Hills, IL (US); Aquilur Rahman, Potomac, MD (US)

(73) Assignee: NeoPharm, Inc., Lake Bluff, IL (US)

( * ) Notice: Subject to any disclaimer, the term of this patent is extended or adjusted under 35 U.S.C. 154(b) by 457 days.

(21) Appl. No.: 10/424,258

(22) Filed: Apr. 28, 2003

(65) Prior Publication Data

US 2003/0215492 A1 Nov. 20, 2003

Related U.S. Application Data

(63) Continuation of application No. PCT/US01/43325, filed on Nov. 9, 2001.

(60) Provisional application No. 60/247,306, filed on Nov. 9, 2000.

(51) Int. Cl.
*A61K 9/127* (2006.01)
(52) U.S. Cl. .......................... 424/450; 264/4.1; 264/4.3
(58) Field of Classification Search .................. 424/450
See application file for complete search history.

(56) References Cited

U.S. PATENT DOCUMENTS

| | | | |
|---|---|---|---|
| 3,993,754 A | 11/1976 | Rahman et al. | |
| 4,008,209 A | 2/1977 | Fujino et al. | |
| 4,016,100 A | 4/1977 | Suzuki et al. | |
| 4,115,544 A | 9/1978 | Shell | |
| 4,224,179 A | 9/1980 | Schneider | |
| 4,229,360 A | 10/1980 | Schneider et al. | |
| 4,235,871 A | 11/1980 | Papahadjopoulos et al. | |
| 4,263,428 A | 4/1981 | Apple et al. | |
| 4,311,712 A | 1/1982 | Evans et al. | |
| 4,348,384 A | 9/1982 | Horikoshi et al. | |
| 4,370,349 A | 1/1983 | Evans et al. | |
| 4,396,630 A | 8/1983 | Riedl et al. | |
| 4,411,894 A | 10/1983 | Schrank et al. | |
| 4,419,348 A | 12/1983 | Rahman et al. | |
| 4,473,692 A | 9/1984 | Miyasaka et al. | |
| 4,515,736 A | 5/1985 | Deamer | |
| 4,522,803 A | 6/1985 | Lenk et al. | |
| 4,545,880 A | 10/1985 | Miyasaka et al. | |
| 4,610,868 A | 9/1986 | Fountain et al. | |
| 4,721,612 A | 1/1988 | Janoff et al. | |
| 4,812,312 A | 3/1989 | Lopez-Berestein et al. | |
| 4,857,319 A | 8/1989 | Crowe et al. | |
| 4,952,408 A | 8/1990 | Rahman | |
| 4,981,968 A | 1/1991 | Wall et al. | |
| 5,003,097 A | 3/1991 | Beaucage et al. | |
| 5,023,087 A | 6/1991 | Yau-Young | |
| 5,077,057 A | 12/1991 | Szoka, Jr. | |
| 5,112,837 A | 5/1992 | Burrows et al. | |
| 5,145,684 A | 9/1992 | Liversidge et al. | |
| 5,162,532 A | 11/1992 | Comins et al. | |
| 5,187,167 A | 2/1993 | Hughes | |
| 5,247,089 A | 9/1993 | Comins et al. | |
| 5,264,423 A | 11/1993 | Cohen et al. | |
| 5,276,019 A | 1/1994 | Cohen et al. | |
| 5,286,717 A | 2/1994 | Cohen et al. | |
| 5,352,789 A | 10/1994 | Hinz | |
| 5,389,377 A | 2/1995 | Chagnon et al. | |
| 5,391,745 A | 2/1995 | Danishefsky et al. | |
| 5,415,867 A | 5/1995 | Minchey et al. | |
| 5,422,344 A | 6/1995 | Priel et al. | |
| 5,424,073 A | 6/1995 | Rahman et al. | |
| 5,447,936 A | 9/1995 | Hausheer et al. | |
| 5,468,859 A | 11/1995 | Fortunak et al. | |
| 5,475,108 A | 12/1995 | Comins et al. | |
| 5,496,830 A | 3/1996 | Shapiro et al. | |
| 5,504,102 A | 4/1996 | Agharkar et al. | |
| 5,527,913 A | 6/1996 | Hinz | |
| 5,541,327 A | 7/1996 | Danishefsky et al. | |
| 5,552,154 A | 9/1996 | Giovanella et al. | |
| 5,552,156 A | 9/1996 | Burke | |
| 5,560,923 A | 10/1996 | Rahman et al. | |

(Continued)

FOREIGN PATENT DOCUMENTS

EP 0 288 255 A2 10/1988

(Continued)

OTHER PUBLICATIONS

Akhtar et al., "Liposome delivery of antisense oligonucleotides: adsorption and efflux characteristics of phosphorothioate oligodeoxynucleutides," *J. of Controlled Release*, 22, 47-56 (1992).
Allen et al., "Liposomes with prolonged circulation times: factors affecting uptake by reticuloendothelial and other tissues," *nBiochimica et Biophysica Acta*, 981, 27-35 (1988).
Allen et al., "Stealth Liposomes: Am Improved Sustained Release System for 1-β-D-Arabinofuranosylcytosine," *Cancer Research*, 52, 2431-2439 (1992)
Blume et al., "Liposomes for the sustained drug release in vivo," *Biochimica et Biophysical Acta*, 1029, 91-97 (1990).
Burke et al., "Lipid Bilayer Partitioning and Stability of Camptothecin Drugs," *Biochemistry*, 32, 5352-5364 (1993).
Burke, et al., "Liposomal Stabilization of Camptothecin's Lactone Ring," *J. Am. Chem. Soc.*, 114, 8318-8319 (1992).
Burris et al., "Activity of Topotecan, a New Topoisomerase I Inhibitor, Against Human Tumor Colony-Forming Units In Vitro," *J. of the Nat. Cancer Institute*, vol. 84, No. 23, 1816-1820 (1992).
Cecil Textbook of Medicine, 15th Edition, vol. 1, 396-399, 475-479 and 817-821 (1997).

(Continued)

*Primary Examiner*—Gollamudi Kishore
(74) *Attorney, Agent, or Firm*—Larisa R. Lacis

(57) ABSTRACT

The present invention is for novel compositions and methods for treating diseases caused by cellular proliferation, particularly, for treating cancer in mammals and more particularly in humans. The therapeutic compositions of the present invention include SN-38 lipid complexes in which the complexes can contain any of a variety of neutral or charged lipids and, desirably, cardiolipin. The compositions are capable of efficiently incorporating SN-38 into complexes and are capable of solubilizing relatively high concentrations of SN-38.

14 Claims, No Drawings

U.S. PATENT DOCUMENTS

| | | | |
|---|---|---|---|
| 5,608,066 A | 3/1997 | Hinz | |
| 5,616,334 A | 4/1997 | Janoff et al. | |
| 5,620,689 A * | 4/1997 | Allen et al. | 424/178.1 |
| 5,622,959 A | 4/1997 | Priel et al. | |
| 5,648,090 A * | 7/1997 | Rahman et al. | 424/450 |
| 5,651,986 A | 7/1997 | Brem et al. | |
| 5,652,244 A | 7/1997 | Giovanella et al. | |
| 5,665,710 A | 9/1997 | Rahman et al. | |
| 5,674,873 A | 10/1997 | Hausheer et al. | |
| 5,674,874 A | 10/1997 | Hausheer et al. | |
| 5,726,181 A | 3/1998 | Hausheer et al. | |
| 5,736,156 A | 4/1998 | Burke | |
| 5,759,767 A | 6/1998 | Lakowicz et al. | |
| 5,776,486 A | 7/1998 | Castor et al. | |
| 5,776,743 A | 7/1998 | Frisch | |
| 5,786,344 A | 7/1998 | Ratain et al. | |
| 5,834,012 A | 11/1998 | Perez-Soler et al. | |
| 5,837,282 A | 11/1998 | Fenske et al. | |
| 5,837,673 A | 11/1998 | Tsujihara et al. | |
| 5,846,565 A | 12/1998 | Brem et al. | |
| 5,859,022 A | 1/1999 | Hausheer et al. | |
| 5,859,023 A | 1/1999 | Hausheer et al. | |
| 5,880,133 A | 3/1999 | Hausheer et al. | |
| 5,882,679 A | 3/1999 | Needham | |
| 5,889,017 A | 3/1999 | Giovanella et al. | |
| 5,900,419 A | 5/1999 | Hausheer et al. | |
| 5,916,596 A | 6/1999 | Desai et al. | |
| 5,948,750 A | 9/1999 | Garsky et al. | |
| 5,955,467 A | 9/1999 | Hausheer et al. | |
| 5,958,937 A | 9/1999 | Hausheer et al. | |
| 5,962,216 A | 10/1999 | Trouet et al. | |
| 5,965,519 A | 10/1999 | Yatvin et al. | |
| 5,972,955 A | 10/1999 | Duvvuri et al. | |
| 5,985,888 A | 11/1999 | Wall et al. | |
| 5,998,426 A | 12/1999 | Bedeschi et al. | |
| 6,015,901 A | 1/2000 | Kawaguchi et al. | |
| 6,046,159 A | 4/2000 | Hausheer et al. | |
| 6,056,973 A | 5/2000 | Allen et al. | |
| 6,057,361 A | 5/2000 | Hausheer et al. | |
| 6,066,645 A | 5/2000 | Hausheer et al. | |
| 6,069,134 A | 5/2000 | Roth et al. | |
| 6,090,407 A | 7/2000 | Knight et al. | |
| 6,096,336 A | 8/2000 | Cao et al. | |
| 6,126,965 A | 10/2000 | Kasid et al. | |
| 6,146,659 A | 11/2000 | Rahman | |
| 6,183,958 B1 | 2/2001 | Stanton, Jr. | |
| 6,214,388 B1 | 4/2001 | Benz et al. | |
| 6,291,175 B1 | 9/2001 | Sévigny et al. | |
| 6,291,676 B1 | 9/2001 | Burke et al. | |
| 6,333,314 B1 | 12/2001 | Kasid et al. | |
| 6,355,268 B1 | 3/2002 | Slater et al. | |
| 6,368,797 B1 | 4/2002 | Schappert | |
| 6,395,481 B1 | 5/2002 | Di Rienzo et al. | |
| 6,461,637 B1 | 10/2002 | Rahman | |
| 6,475,736 B1 | 11/2002 | Stanton, Jr. et al. | |
| 6,495,579 B1 * | 12/2002 | Hunter | 514/365 |
| 6,500,650 B1 | 12/2002 | Stanton, Jr. et al. | |
| 6,537,759 B1 | 3/2003 | Stanton, Jr. et al. | |
| 6,548,071 B1 | 4/2003 | Cherian | |
| 6,559,129 B1 | 5/2003 | Kasid et al. | |
| 6,573,049 B1 | 6/2003 | Schappert | |
| 6,582,923 B2 | 6/2003 | Stanton, Jr. et al. | |
| 6,610,492 B1 | 8/2003 | Stanton, Jr. et al. | |
| 6,664,062 B1 | 12/2003 | Stanton, Jr. | |
| 6,740,335 B1 | 5/2004 | Moynihan et al. | |
| 2002/0103141 A1 | 8/2002 | McKearn et al. | |
| 2002/0119990 A1 | 8/2002 | Madden et al. | |
| 2002/0150943 A1 | 10/2002 | Stanton, Jr. et al. | |
| 2003/0073123 A1 | 4/2003 | Shen et al. | |
| 2003/0215489 A1 | 11/2003 | Kasid et al. | |
| 2003/0219476 A1 | 11/2003 | Ahmad et al. | |
| 2003/0225023 A1 | 12/2003 | Kasid et al. | |
| 2003/0228317 A1 | 12/2003 | Gokhale et al. | |
| 2003/0229040 A1 | 12/2003 | Kasid et al. | |
| 2004/0005603 A1 | 1/2004 | Kasid et al. | |
| 2004/0082771 A1 | 4/2004 | Kasid et al. | |
| 2004/0106571 A1 | 6/2004 | Kasid et al. | |
| 2004/0115714 A1 | 6/2004 | Kasid et al. | |
| 2004/0248218 A1 | 12/2004 | Kasid et al. | |
| 2005/0002918 A1 | 1/2005 | Strauss et al. | |
| 2005/0019387 A1 | 1/2005 | Rahman et al. | |
| 2005/0148528 A1 | 7/2005 | Gately | |
| 2005/0153297 A1 | 7/2005 | Ahmad et al. | |
| 2005/0181037 A1 | 8/2005 | Ahmad et al. | |
| 2005/0202074 A9 | 9/2005 | Rahman | |
| 2005/0238706 A1 | 10/2005 | Ahmad et al. | |
| 2005/0249795 A1 | 11/2005 | Zhang et al. | |
| 2005/0266068 A1 | 12/2005 | Ahmad et al. | |
| 2005/0277611 A1 | 12/2005 | Ahmad et al. | |

FOREIGN PATENT DOCUMENTS

| | | | |
|---|---|---|---|
| EP | 1 352 970 A1 | 10/2003 | |
| SU | 629927 A | 10/1978 | |
| SU | 1186212 A | 10/1985 | |
| WO | WO 83/03383 A1 | 10/1983 | |
| WO | WO 86/01103 A1 | 2/1986 | |
| WO | WO 93/18751 A1 | 9/1993 | |
| WO | 95/08986 | * | 4/1995 |
| WO | WO 95/08386 A1 | 4/1995 | |
| WO | WO 95/08986 A1 | 4/1995 | |
| WO | WO 96/11669 A1 | 4/1996 | |
| WO | WO 98/17256 A1 | 4/1998 | |
| WO | WO 98/43095 A | 10/1998 | |
| WO | WO 99/13816 A2 | 3/1999 | |
| WO | WO 99/51202 A2 | 10/1999 | |
| WO | WO 00/01366 A | 1/2000 | |
| WO | WO 00/23052 A1 | 4/2000 | |
| WO | WO 00/50639 A | 8/2000 | |
| WO | WO 00/52210 A | 9/2000 | |
| WO | WO 01/53460 A | 7/2001 | |
| WO | WO 01/70220 A | 9/2001 | |
| WO | WO 02/00168 A2 | 1/2002 | |
| WO | WO 02/32400 A | 4/2002 | |
| WO | WO 02/059337 A | 8/2002 | |
| WO | WO 02/081639 A | 10/2002 | |
| WO | WO 02/081640 A | 10/2002 | |
| WO | WO 02/081641 A | 10/2002 | |
| WO | WO 02/081642 A | 10/2002 | |
| WO | WO 02/088714 A | 11/2002 | |
| WO | WO 03/013536 A | 2/2003 | |
| WO | WO 03/013537 A | 2/2003 | |
| WO | WO 03/018018 A | 3/2003 | |
| WO | WO 03/030864 A1 | 4/2003 | |
| WO | WO 03/039600 A | 5/2003 | |
| WO | WO 02/058622 A2 | 8/2003 | |
| WO | WO 03/070221 A | 8/2003 | |
| WO | WO 03/099213 A | 12/2003 | |
| WO | WO 03/099830 A | 12/2003 | |
| WO | WO 03/102011 A | 12/2003 | |
| WO | WO 03/103596 A2 | 12/2003 | |
| WO | WO 2004/017940 A3 | 3/2004 | |
| WO | WO 2004/017944 A | 3/2004 | |
| WO | WO 2004/035032 A2 | 4/2004 | |
| WO | WO 2004/035523 A | 4/2004 | |
| WO | WO 2004/039817 A | 5/2004 | |
| WO | WO 2004/062569 A | 7/2004 | |
| WO | WO 2004/069224 A | 8/2004 | |
| WO | WO 2004/071466 A | 8/2004 | |
| WO | WO 2004/087758 A | 10/2004 | |
| WO | WO 2005/000266 A | 1/2005 | |
| WO | WO 2005/000318 A | 1/2005 | |
| WO | WO 2005/042028 A | 5/2005 | |

WO WO 2005/067632 A 7/2005

OTHER PUBLICATIONS

Clements et al., "Antiangiogenic potential of camptothecin and Chakrabarti et al., "Generation of characterization of iron- and barium-loaded liposomes," *Biochimica et Biophysica Acta*, 1108, 233-239 (1992). topotecan," *Cancer Chemother Pharmacol*, 44, 411-416 (1999).
Crommelin et al., "Stability of Liposomes on Storage: Freeze Dried, Frozen or as an Aqueous Dispersion," *Pharm. Research*, 3, 159-163 (1984).
Crowe et al., "Infrared Spectroscopic Studies on Interactions of Water and Carbohydrates with a Biological Membrane," *Archives of Biochem. And Biophysics*, vol. 232, No. 1, 400-407 (1984).
Crowe et al., "Preservation of Structural and Functional Activity in Lyophilized Sarcoplasmic Reticulum," *Archives of Biochem. And Biophysics*, vol. 220, No. 2, 477-484 (1983).
Crowe et al., "Preservation of Freeze-Dried Liposomes by Trehalose," *Archives Biochem. And Biophysics*, vol. 242, No. 1, 240-247 (1985).
Crowe et al., "Interactions of Phospholipid Monolayers with Carbohydrates," *Biochimica et Biophysica*, vol. 769, 151-159 (1984).
Crowe et al., "Effects of Carbohydrates on Membrane Stability at Low Water Activities," *Archives Biochem. And Biophysics*, vol. 769, 141-150 (1984).
Daoud et al., "Modulation of Doxorubicin Resistance by Valinomycin (NSC 122023) and Liposomal Valinomycin in Chinese Hamster Ovary Cells," *Cancer Research*, 49, 2661-2667 (1989).
Deamer et al., "Liposome Preparation: Methods and Mechanisms," 27-51.
Druckmann et al., "Separation of liposome-associated doxorubicin in human plasma: implications for pharmacokinetic studies," *Archives Biochem. And Biophysics*, 980, 381-384 (1989).
Emerson et al., "In Vivo Antitumor Activity of Two New Seven-substituted Water-soluble Campotothecin Analogues," *Cancer Research*, 55, 603-609 (1995).
Erickson-Miller et al., "Differential toxicity of camptothecin, topotecan and 9-aminocamptothecin to human, canine, and murine myeloid progenitors (CFU-GM) in vitro," *Cancer Chemother Pharmacol*, 39, 467-472 (1997).
Fan et al., "Enhancement of Murine Tumor Cell Sensitivity to Adriamycin by Presentation of the Drug in Phosphatidylcholine-Phosphatidylserine Liposomes," *Cancer Research*, 50, 3619-3626 (1990).
Forssen et al., "Selective in Vivo Localization of Daunorubicin Small Unilamellar Vesicles in-Solid Tumors," *Cancer Research*, 52, 3255-3261 (1992).
Forssen et al., "Improved Therapeutic Benefits of Doxorubicin by Entrapment in Anionic Liposomes," *Cancer Research*, 43, 546-550 (1983).
Forssen et al., "In Vitro and In Vivo Studies with Adriamycin Liposomes," *Biochem. And Biophysical Research Communications*, vol. 91, No. 4 (1979).
Fry et al., "Rapid Separation of Low Molecular Weigth Solutes from Liposomes without Dilution," *Analytical Biochem.*, 90, 809-815 (1978).
Gabizon et al., "Liposome formulations with prolonged circulation time in blood and enhanced uptake by tumors," *Proc. Natl. Acad. Sci.*, 85, 6949-6953 (1988).
Gabizon et al., "Effect of Liposome Composition and Other Factors on the Targeting of Liposomes to Experimental Tumors: Biodistribution and Imaging Studies," *Cancer Research*, 50, 6371-6378 (1990).
Garcia-Carbonero et al., "Current Perspectives on the Clinical Experience, Pharmacology, and Continued Development of the Camptothecins," *Clinical Cancer Research*, 8, 641-661 (2002).
Giovanella et al., "Complete Growth Inhibition of Human Cancer Xenografts in Nude Mice by Treatment with 20-(S)-Camptothecin," *Cancer Research*, 51, 3052-3055 (1991).
Giovanella et al., "DNA Topoisomerase I-Targeted Chemotherapy of Human Colon Cancer in Xenografts," *Science*, 246, 1046-1048 (1989).

Green Cross Corp., "Blood coagulation factor XIII preparations for oral administration," *Chem. Abs.*, 97:11851g (1982).
Gregoriadis et al., "The Carrier Potential of Liposomes in Biology and Medicine," *The New England Journal of Medicine*, 295(12), 704-710 (1976).
Grochow et al., "Pharmacokinetics and Pharmacodynamics of Topotecan in Patients with Advanced Cancer," *Drug Metabolism and Disposition*, vol. 20, No. 5, 706-713 (1992).
Hardman et al., "Efficacy of Treatment of Colon, Lung and Breast Human Carcinoma Xenografts with: Doxorubicin, Cisplatin, Irinotecan or Topotecan," *Anticancer Research*, 19, 2269-2274 (1999).
Hillery, "Supramolecular lipidic drug delivery systems: From laboratory to clinic A review of the recently introduced commercial liposomal and lipid-based formulations of amphotericin B," *Advanced Drug Delivery Reviews*, 24, 345-363 (1997).
Hong et al., "Formulation, stability, and antitumor activity of 1-beta-D-arabinofuranosylcytosine conjugate of thioether phospholipid," *Cancer Research*, Computer Search Listing Abstract (1990).
Hong et al., "Nucleoside conjugates. 11. Synthesis and antitumor activity of 1-beta-D-arabinofuranosylcytosine and cytidine conjugates of thioether lipids," *J. Med. Chem.*, Computer Search Listing Abstract (1990).
Hsiang et al., "Identification of Mammalian DNA Topoisomerase I as an Intracellular Target of the Anticancer Drug Camptothecin," *Cancer Research*, 48, 1722-1726 (1988).
Huang et al., "Microscopic Localization of Sterically Stabilized Liposomes in Colon Carcinoma-bearing Mice," *Cancer Research*, 52, 5135-5143 (1992).
Janoff et al., "Amphotericin B Lipid Complex (ABLC): A Molecular Rationale for the Attenuation of Amphotericin B Related Toxicities," *J. of Liposomes Research*, 3(3), 451-471 (1993).
Jansen et al., "CPT-11 In Human Colon-Cancer Cell Lines and Xenografts: Characterization of Cellular Sensitivity Determinants," *Int. J. Cancer*, 70, 335-340 (1997).
Jett et al., "Tumoricidal Effects of Liposomes Containing Phosphatidylinositol or Phosphatidylcholine," *Biochem. Biophys. Res. Commun.*, 114, 459-466 (1983).
Killion et al., (Augmentation of Amtiproliferative Activity of Interferon Alfa Against Human Bladder Tumor Cell-Lines by Encapsulation of Interferon Alfa within Liposomes, *J. Nat. Cancer Institute*, 81(18), 1387-1392 (1989).
Knotting et al., "Alkylphosphocholines: influence of structural variation on biodistribution at antineoplastically active concentrations," *Cancer-Chemother-Pharmacol.*, Computer Search Listing Abstract (1992).
Lasic, "Liposomes: Synthetic lipid microspheres serve as multipurpose vehicles for the delivery of drugs, genetic material and cosmetics," *American Scientist*, 80, 20-31 (1992).
Lasic, "Mixed Micelles in Drug Delivery," *Nature*, 355(6357), 272-280 (1992).
Machy et al., "Small Liposomes are better than large liposomes for specific drug delivery in vitro," *Biochimica et Biophysica Acta.*, 730, 313-320 (1983).
Madden et al., "Protection of large unilamellar vesicles by trehalose during dehydration: retention of vesicle contents," *Biochimica et Biophysica Acta.*, 817, 67-74 (1985).
Madden et al., "Encapsulation of Topotecan in Lipid-Based Carrier Systems. Evaluation of Drug Stability and Plasma Elimination in a Murine Model, and Comparison of Antitumor Efficacy Against Murine L1210 and B16," *Proc. Of ASCO*, 17:abstract #754 (1998).
Madden et al., "The accumulation of drugs within large unilamellar vesicles exhibiting a proton gradient a survey," *Chemistry and Physics of Lipids*, 53, 37-46 (1990).
Margalit et al., "Liposomal drug delivery: thermodynamic and chemical kinetic considerations," *J. of Controlled Release*, 17, 285-296 (1991).
Mathijssen et al., "Clinical Pharmacokinetics and Metabolism of Irinotecan," *Clinical Cancer Research*, 7, 2182-2194 (2001).
Mayer et al., "Characterization of liposomal systems containing doxorubicin entrapped in response to pH gradients," *Biochimica et Biophysica Acta.*, 1025, 143-151 (1990).

Mayer et al., "Influence of Vesicle Size, Lipid Composition, and Drug-to-Lipid Ratio on the Biological Activity of Liposomal Doxorubicin in Mice," *Cancer Research*, 49, 5922-5930 (1989).

McCabe et al., "Comparative Activity of Oral and Parenteral Topotecan in Murine Tumor Models: Efficacy of Oral Topotecan," *Cancer Investigation*, 12(3), 308-313 (1994).

Okuno et al., "Complete Regression of Xenografted Human Carcinomas by Camptothecin Analogue-Carboxymethyl Dextran Conjugate (T-0128)," *Cancer Research*, 60, 2988-2995 (2000).

O'Leary et al., "Antiangiogenic Effects of Camptothecin Analogues 9-Amino-20(S)-camptothecin, Topotecan, and CPT-11 Studied in the Mouse Cornea Model," *Clinical Cancer Research*, 5, 181-187 (1999).

Olitzki, "Immunological Methods in Brucellosis Research, Part II: In vivo *Procedures*," Bibliotheca Microbiologica, No. 9, 196-203 (1970).

Ormrod et al., "Topotecan: A Review of its Efficacy in Small Cell Lung Cancer," *ADIS Drug Evaluation*, 58(3), 534-551 (1999).

Ostro, "Liposomes in the Diagnosis and Treatment of Cancer," *Liposomes From Biophysics to Therapeutic*, 277-339 (1987).

Pagano, "Interatctions of Liposomes with Mammalian Cells," *Ann. Rev. Biophys. Bioeng.*, 7, 435-468 (1978).

Palmisano et al., "Determination of methotrexate in untreated body fluids by micellar liquid chromatography," *Anal-Chem.*, Computer Listing Search Abstract, (1989).

Pantazis et al., "Complete Inhibition of Growth followed by Death of Human Malignant Melanoma Cells in Vitro and Regression of Human Melanoma Xenografts in Immunodeficient Mice Induced by Camptothecins," *Cancer Research*, 52, 3980-3987 (1992).

Papahadjopoulos et al., "Sterically stabilized liposomes: Improvements in pharmacokinetics and antitumor therapeutic efficacy," *Proc. Natl. Acad. Sci.*, 88, 11460-11464 (1991).

Partearroyo et al., "Effective detergent/lipid ratios in the solubilization of phosphatidylcholine vesicles by Triton X-100," 302(2), 138-140 (1992).

Pejaver et al., "The Role of Liposome Composition on the Stabilization of Ancitabine," *Drug Development and Industrial Pharmacy*, 13(15), 2633-2649 (1987).

Perez-Soler et al., "Phase I Clinical and Pharmacological Study of Liposome-entrapped cis-Bis-neodecanoato-trans-R,R-1,2-diaminocyclohexane Platinum(II)," *Cancer Research*, 50, 4254-4259 (1990).

R. Perez-Solar, "Liposomes as Carries of Antitumor Agents: Toward a Clinical Realty," *Cancer Treatment Reviews*, 16, 67-82 (1989).

Potmesil et al., "Preclinical Studies of DNA Topoisomerase I-Targeted 9-Amino and 10, 11 Methylenedioxy Camptothecins," *DNA Topoisomerases Cancer*, Chemical Abstract No. 103,369, vol. 117 (1991).

Pinnaduwage et al., "Stable Target-Sensitive Immunoliposomes," *Biochemistry*, 31, 2850-2855 (1992).

Racker, "Reconstitution of Cytochrome Oxidase Vesicles and Conferral of Sensitivity to Energy Transfer Inhibitors," *J. Membrane Biol.*, 10, 221-235 (1972).

Rahman et al., "Anti-Laminin Receptor Antibody Targeting of Liposomes With Encapsulated Doxorubincin to Human Breast Cancer Cells In Vitro," *J. of the Nat. Cancer Institute*, 81(23), 1794-1800 (1989).

Rahman et al., "Pharmacological, Toxicological, and Therapeutic Evaluation in Mice of Doxorubicin Entrapped in Cardiolipin Liposomes," *Cancer Research*, 45, 796-803 (1985).

Rieger, "Surfactants," *Pharmaceutical Dosage Forms Disperse System*, 1(8), 334-338 (1988).

Y. Sadzuka, "Effective Prodrug Liposome and Conversion to Active Metabolite," *Current Drug Metabolism*, 1, 31-48 (2000).

Sadzuka et al., "Effect of liposomalization on the antitumor activity, side-effects and tissue distribution of CPT-11," *Cancer Letters*, 127, 99-106 (1998).

Senior et al., "Interaction of Positively-charged Liposomes with Blood: Implications for their applications in vivo," *Biochimica et Biophysical Act*, 1070, 173-179 (1991).

Shelly et al., "Model studies directed toward the boron neutron-capture therapy of cancer: Boron delivery to murine tumors with liposomes," *Proc. Natl. Acad. Sci. USA*, 89, 9039-9043 (1992).

Shulkin et al., "Lyophilized liposomes: a new method for long-term vesicular storage," *J. Microencapsul.*, 1(1), 73-80 (1984).

Storm et al., "Influencing of Lipid Composition on the Antitumor Activity Exerted by Doxorubicin-containing Liposomes in a Rat Solid Tumor Model," *Cancer Research*, 47, 3366-3372 (1987).

Sugaman et al., "Lipid-complexed camptothecin: Formulation and initial biodistribution and antitumor activity studies," *1-Pharmacology*, Chemical Abstract No. 124:332078g, 124(25), 94 (1996).

Supersaxo et al., "Mixed Micelles as a Proliposomal Lymphotropic Drug Carrier," *Pharmaceutical Research*, 8(10), 1286-1291 (1991).

Szoka, "Comparative Properties and Methods of Preparation of Lipid Vesicles (Liposomes)," *Ann. Rev. Biophys. Bioeng.*, 9, 467-508 (1980).

Szoka et al., "Procedure for preparation of liposomes with large internal aqueous space and high capture by reverse-phase evaporation," *Proc. Natl. Acad. Sci. USA*, 75(9), 4194-4198 (1978).

Tardi et al., "Liposomal Encapsulation of Topotecan Enhances Anti-cancer Efficacy in Murine and Human Xenograft Models," *Cancer Research*, 60, 3389-3393 (2000).

Thies et al., "Method for Rapid Separation of Liposome-Associated Doxorubicin from Free Doxorubicin in Plasma," *Analytical Biochem.*, 188, 65-71 (1990).

Thompson et al., "Animal models for studying the action of topoisomerase I targeted drugs," *Biochimica et Biophysica Acta*, 1400, 301-319 (1998).

Topchieva et al., "Block copolymers of ethylene oxide and propylene oxide (pluronics) as immunomodulators and antitumor agents," *Biomed-Sci.*, Computer Listing Search Abstract, (1991).

Tsyganenko et al., *Antibiotiki*, 28(8), 577-581 (1983) Russian.

Usov et al., "Structure and antitumor activity of polysaccharides from the micelles of *Aspergillus oryzae*," *Bioorg-Khim*, Computer Listing Search Abstracts, (1991).

Vion-Dury et al., "Liposome-Mediated Delivery of Gadolinium-Diethylenetraminopentaacetic Acid to Hepatic Cells," *J. Pharm. And Exp. Therapeutics*, 250(3), 1113-1119 (1989).

Wall et al., "Plant Antitumor Agents. I. The Isolation and Structure of Camptothecin, a Novel Alkaloidal Leukemia and Tumor Inhibitor from *Camtotheca acuminata*," *J. of the American Chem. Soc.*, 88(16), 3888-3890 (1966).

Weinstein, "Liposomes in the Diagnosis and Treatment of Cancer," 9, 277-338.

Woodle et al., "Liposome Preparation and Size Characterization," *Methods in Enzymology*, 71, 193-217 (1989).

Wu et al., "In vitro studies on adsorbents employed in artificial liver, artificial kidney and blood detoxifier. III. Adsorptive properties and efficiency of domestic neutral macroreticular resins," *Chemical Abstracts*, 99:163963z (1983).

Yokoyama et al., "Toxicity and antitumor activity against solid tumors of micelle-forming polymeric anticancer drug and its extremely long circulation in blood," *Cancer-Res.*, Computer Listing Search Abstract, (1991).

U.S. Appl. No. 10/165,867, filed Jun. 6, 2002, Unger et al.

U.S. Appl. No. 10/457,068, filed Jun. 5, 2003, Unger et al.

Emerson, D. L., "Liposomal delivery of camptothecins," *Pharm. Sci. and Tech. Today*, 3, 205-209 (2000).

Innocenti et al., "Pharmacogentics of anticancer agents: Lessons from amonafide and irinotecan," *Drug Metabolism and Disposition*, 29, 596-600 (2001).

Pizzolato et al., "The camptothecins," *The Lancet*, 361, 2235-2242 (2003).

U.S. Appl. No. 11/061,044, filed Feb. 18, 2005, Ahmad et al.

U.S. Appl. No. 60/247,306, filed Nov. 9, 2000, Rahman et al.

U.S. Appl. No. 60/294,285, filed May 29, 2001, Rahman et al.

U.S. Appl. No. 60/404,668, filed Aug. 20, 2002, Rahman et al.

Cavaletti et al., *Toxicology Letters*, 118: 103-107 (2000).

Gokhale et al., *British Journal of Cancer*, 74: 43-48 (1996).

Guichard et al., *Clinical Cancer Research*, 4: 3089-3094 (Dec. 1998).

Hardman et al., *British Journal of Cancer*, 81(3): 440-8 (Oct. 1999).

Kawato et al., *Cancer Research*, 51(16): 4187-91 (Aug. 15, 1991).

Kawato et al., *Cancer Chemotherapy and Pharmacology*, 28(3): 192-198 (1991).

Lavelle et al., *Seminars in Oncology* 23(1) Suppl.3: 11-20 (Feb. 1996).

Lundberg, *Anti-Cancer Drug Design*, 13: 453-461 (1998).
Machida et al., *Journal of Controlled Release*, 66: 159-175 (2000).
Monks et al., *Journal of the National Cancer Institute*, (83(11): 757-766 (Jun. 5, 1991).
Ratain et al., *Journal of Clinical Oncology*, 20(1): 7-8 (Jan. 1, 2002).
Wadkins et al., *Cancer Research*, 59(14): 3424-8 (Jul. 15, 1999).
Williams et al., *J. Controlled Release*, 91: 167-172 (2003).
U.S. Appl. No. 09/354,109, filed Jul. 15, 1999, Kasid et al.
U.S. Appl. No. 09/930,283, filed Aug. 16, 2001, Kasid et al.
U.S. Appl. No. 10/056,210, filed Jan. 28, 2002, Kasid et al.
U.S. Appl. No. 10/239,598, filed Oct. 25, 2000, Rahman.
U.S. Appl. No. 10/680,313, filed Oct. 6, 2003, Kasid et al.
U.S. Appl. No. 10/786,866, filed Feb. 24, 2004, Zhang et al.
U.S. Appl. No. 11/010,158, filed Dec. 10, 2004, Kasid et al.
U.S. Appl. No. 11/105,970, filed Apr. 14, 2005, Ahmad et al.
U.S. Appl. No. 11/106,406, filed Apr. 14, 2005, Ahmad et al.
U.S. Appl. No. 11/177,194, filed Jul. 8, 2005, Ahmad et al.
U.S. Appl. No. 11/196,123, filed Aug. 3, 2005, Zhang et al.
U.S. Appl. No. 11/201,810, filed Aug. 11, 2005, Bhamidipati et al.
U.S. Appl. No. 11/220,888, filed Sep. 7, 2005, Gately et al.
U.S. Appl. No. 11/287,530, filed Nov. 22, 2005, Jamil et al.
U.S. Appl. No. 60/041,192, filed Mar. 21, 1997, Kasid et al.
U.S. Appl. No. 60/241,069, filed Oct. 16, 2000, Rahman et al.
U.S. Appl. No. 60/264,062, filed Jan. 26, 2001, Kumar et al.
U.S. Appl. No. 60/281,779, filed Apr. 6, 2001, Kasid et al.
U.S. Appl. No. 60/281,780, filed Apr. 6, 2001, Kasid et al.
U.S. Appl. No. 60/281,785, filed Apr. 6, 2001, Kasid.
U.S. Appl. No. 60/281,796, filed Apr. 6, 2001, Kasid et al.
U.S. Appl. No. 60/314,959, filed Aug. 24, 2001, Rahman et al.
U.S. Appl. No. 60/332,477, filed Nov. 9, 2001, Strauss et al.
U.S. Appl. No. 60/371,116, filed Apr. 10,2002, Kasid et al.
U.S. Appl. No. 60/371,126, filed Apr. 10, 2002, Kasid et al.
U.S. Appl. No. 60/382,031, filed May 22, 2002, Gokhale et al.
U.S. Appl. No. 60/382,411, filed May 20, 2002, Gatley.
U.S. Appl. No. 60/383,340, filed May 24, 2002, Ahmad et al.
U.S. Appl. No. 60/384,222, filed May 29,2002, Ahmad et al.
U.S. Appl. No. 60/405,378, filed Aug. 23,2002, Zhang et al.
U.S. Appl. No. 60/419,277, filed Oct. 16,2002, Ahmad et al.
U.S. Appl. No. 60/429,285, filed Nov. 26, 2002, Ahmad et al.
U.S. Appl. No. 60/438,659, filed Jan. 7, 2003, Ahmad et al.
U.S. Appl. No. 60/444,958, filed Feb. 3, 2003, Zhang et al.
U.S. Appl. No. 60/446,895, filed Feb. 11, 2003, Bhamidipati et al.
U.S. Appl. No. 60/446,898, filed Mar. 26, 2003, Gately et al.
U.S. Appl. No. 60/467,331, filed May 2, 2003, Ahmad et al.
U.S. Appl. No. 60/472,664, filed May 22, 2003, Jamil et al.
U.S. Appl. No. 60/480,669, filed Jun. 23, 2003, Jamil et al.
U.S. Appl. No. 60/495,260, filed Aug. 13, 2003, Jamil et al.
U.S. Appl. No. 60/514,658, filed Oct. 27, 2003, Ahmad et al.
U.S. Appl. No. 60/535,042, filed Jan. 7, 2004, Ahmad et al.
U.S. Appl. No. 60/556,843, filed Mar. 27, 2004, Ahmad et al.
U.S. Appl. No. 60/557,232, filed Mar. 29, 2004, Ahmad et al.
U.S. Appl. No. 60/577,414, filed Jun. 5, 2004, Hussey et al.
U.S. Appl. No. 60/583,833, filed Jun. 29, 2004, Ahmad et al.
Office Action mailed Mar. 4, 2005, in U.S. Appl. No. 10/717,378.
Office Action mailed Jul. 7, 2005, in U.S. Appl. No. 10/717,378.
Ando et al., "UGT1A1 genotypes and glucuronidation of SN-38, the active metabolite of irinotecan," *Ann. Oncol.*, 9, 845-847 (1998).
Ando et al., "Polymorphisms of UDP-glucuronosyltransferase gene and irinotecan toxicity: a pharmacogenetic analysis," *Cancer Res.* 60, 6921-6926 (2000).
Bosma et al., "Bilirubin UDP-glucuronosyltransferase 1 is the only relevant bilirubin glucuronidating isoform in man," *J. Biol. Chem.* 269, 17960-17964.
Bosma et al., "The genetic basis of the reduced expression of bilirubin UDP-glucuronosyltransferase 1 in Gilbert's syndrome," *New Engl. J. Med.* 333, 1171-1175 (1995).
Cersosimo et al., "A new antineoplastic agent for the management of colorectal cancer," *Ann. Pharmacother*. 32:1324-1333, (1998).
Drummond et al., "Optimizing Liposomes for Delivery of Chemotherapeutic Agents to Solid Tumors," *Pharmacol. Rev.* 51, 691-743 (1999).
Fishman et al., "Phase I study of Liposomal SN-38 (LE-SN38) in Patients With Advanced Cancer: Pharmacogenomics and Pharmacokinetics," *AARC-NCI-EORTC International Conference on Molecular Targets and Cancer Therapeutics* (Boston, MA), Abstract B250 (Nov. 2003).
Fishman et al., "Phase I study of liposome encapsulated mitoxantrone (LEM) in patients with advanced cancers," *Ann. Oncol.* 13 (Suppl. 5), 23 (2002).
Gilbert et al., "Phase I study of 9-nitrocamptothecin (9-NC) liposome aerosol for the treatment of primary and metastatic cancer to the lungs: effect of dose escalation on bronchoalveolar lavage (BAL) and plasma drug levels," *Proc. Am. Assoc. Cancer Res.*, 43, 430 (Abstract 2138) (2002).
Gupta et al., "Metabolic fate of irinotecan in humans: correlation of glucuronidation with diarrhea," *Cancer Res.* 54, 3723-3725 (1994).
Gutberlet et al., "Cardiolipin, α-D-glucopyranosyl, and L-lysylcardiolipin from Gram-positive bacteria: FAB MS, monifilm and X-ray powder diffraction studies," *Biochim. Biophys. Acta*, 463, 307-322 (2000).
Hecht, "Gastrointestinal toxicity of irinotecan," *Oncology* 12, 72-78 (1998).
Hsiang et al., "Arrest of replication forks by drug-stabilized topoisomerase I-DNA cleavable complexes as a mechanism of cell killing by camptothecin," *Cancer Res.* 49, 5077-5082 (1989).
Hsiang et al., "Camptothecin induces protein-linked DNA breaks via mammalian DNA topoisomerase I," *J. Biol. Chem.* 260, 14873-14878 (1985).
Innocenti et al., "UGT1A1 *28 polymorphism is a predictor of neutropenia in irinotecan chemotherapy," *Proc. Am. Soc. Clin. Oncol.*, 22, 124 (Abstract 495) (2003).
Iyer et al., "Genetic predisposition to the metabolism of irinotecan (CPT-11). Role of uridine diphosphate glucuronosyltransferase isoform 1A1 in the glucuronidation of its active metabolite (SN-38) in human liver microsomes," *J Clin Invest* 101:847-854, (1998).
Iyer et al. "Phenotype-genotype correlation of in vitro SN-38 (active metabolite of irinotecan) and bilirubin glucuronidation in human liver tissue with UGTI A1 promoter polymorphism," *Clin. Pharmacol. Ther.*, 65, 576-582 (1999).
Iyer et al., "UGTIA1 *28 polymorphism as a determinant of irinotecan disposition and toxicity," *Pharmacogenetics*, 2, 43-47 (2002).
Kehrer et al., "Factors involved in prolongation of the terminal disposition phase of SN-38: clinical and experimental studies," *Clin. Cancer Res.*, 6, 3451-3458 (2000).
Knight et al., "Anticancer effect of 9-nitrocamptothecin liposomes aerosol on human cancer xenografts in nude mice," *Cancer Chemother. Pharmacol.*, 44, 177-186 (1999).
Kraut et al., "Pharmacogenomic and pharmacokinetic assessment of liposome encapsulated SN-38 (LE-SN38) in advanced cancer patients," presented at ASCO (American Society of Clinical Oncology), New Orleans, LA, Jun. 5-8, 2004, Abstract 2501 (Jun. 5, 2004).
Kunimoto et al., "Antitumor activity of 7-ethyl-10-[4-(1-piperidino)-1-piperidino]carbonyloxy-camptothecin, a novel water soluble derivative of camptothecin, against murine tumors," *Cancer Res.* 47:5944-5947, (1987).
Lampe et al., "UDP-glucuronosyltransferase (UGT1A1 *28 and UGT1A6*2) polymorphisms in Caucasians and Asians: relationships to serum bilirubin concentrations," *Pharmacogenetics*, 9, 341-349 (1999).
Lavelle et al. "Preclinical evaluation of CPT-11 and its active metabolite SN-38," *Semin. Oncol.*, 23, 11-20 (1996).
Mathijssen et al., "Impact of body-size measures on irinotecan clearance: alternative dosing recommendations," *J. Clin. Oncol.*, 20, 81-87 (2002).
Monaghan et al., "Genetic variation in bilirubin UPD-glucuronosyltransferase gene promoter and Gilbert's syndrome," *Lancet*, 347, 578-581 (1996).
O'Leary et al, "Camptothecins: a review of their development and schedules of administration," *Eur. J. Cancer.*, 34, 1500-1508 (1998).
Osborne, "Nastech licenses RNAi patents to boost tight junctions work," *BioWorld Today*, 15(21), 1, 6 (Feb. 3, 2004).

Pfizer, Inc., Package insert for Camptosar® (Jul. 2005).

Pitot et al, "Phase I dose-finding and pharmacokinetic trial of irinotecan hydrochloride (CPT-11) using a once-every-three-week dosing schedule for patients with advanced solid tumor malignancy," *Clin Cancer Res.*, 6, 2236-2244 (2000).

Rainier et al., "Phase transition characteristics of diphosphatidylglycerol (cardiolipin) and stereoisomeric phosphatidyldiacylglycerol bilayers: mono- and divalent metal ion effects," *Biochim. Biophys. Acta*, 558, 187-198 (1979).

Rivory et al, "Kinetics of the in vivo interconversion of the carboxylate and lactone forms of irinotecan (CPT-11) and of its metabolite SN-38 in patients," *Cancer Res.* 54:6330-6333, (1994).

Rivory et al, "Pharmacokinetic interrelationships of irinotecan (CPT-11) and its-three major plasma metabolites in patients enrolled in phase I/II trials," *Clin. Caner Res.*, 3, 1261-1266 (1997).

Rivory, "Metabolism of CPT-11 impact on activity," *Ann. N. Y. Acad. Sci.*, 922, 205-215 (2000).

Rothenberg, "Topoisomerase I inhibitors: review and update," *Ann. Oncol.* 8:837-855, (1997).

Sanghani et al., "Carboxylesterases expressed in human colon tumor tissue and their role in CPT-11 hydrolysis," *Clin. Cancer Res.*, 9(13), 4983-4991 (Oct. 15, 2003).

Sasaki et al., "Pharmacological correlation between total drug concentration and lactones of CPT-11 and SN-38 in patients treated with CPT-11," *Cancer Res.*, 86, 111-116 (1995).

Schaeppi et al., "Toxicity of camptothecin (NSC-100880)," *Cancer Chemother. Rep.*, 5, 25-36 (1974).

Slatter et al., "Pharmacokinetics, metabolism and excretion of irinotecan (CPT-11) following iv infusion of [14C]CPT-11 in cancer patients," *Drug Metab. Dispos.*, 28, 423-433 (2000).

Strassburg et al., "Jaundice, genes and promoters," *J. Hepatol.*, 33, 467-479 (2000).

Takimoto et al., "The captothecins," in *The camptothecins. Cancer chemotherapy and biotherapy*, 2nd ed. (Chabner et al., eds.), Chapter 19, 463-484 (Lippincott-Raven, Philadelphia, PA, 1996).

Treat et al., "Phase I trial in advanced malignancies with liposome encapsulated paclitaxel (LEP)," *Clin. Cancer Res.*, 6, 4492s (2000).

Vanhoefer et al., "Irinotecan in the treatment of colorectal cancer: clinical overview," *J. Clin. Oncol.*, 19, 1501-1518 (2001).

Vaughn et al., "A phase I study of a new liposome encapsulated doxorubicin (LED) formulation in advanced malignancies," *Proc. Am. Soc. Clin. Oncol.*, 19 (23), 1a (Abstract 892) (1999).

Wadler et al., "Recommended guidelines for the treatment of chemotherapy-induced diarrhea," *J. Clin. Oncol.*, 16, 3169-3178 (1998).

Wasserman et al., "Severe CPT-1 1 toxicity in patients with Gilbert's syndrome: two case reports," *Ann. Oncol.*, 8, 1049-1051 (1997).

J.Allen Zhang et al, Development and Characterization of a Novel Liposome-Based Formulation of SN-38, International Journal of Pharmaceutics 270 (2004) 93-107.

V.Peikov et al, ph-Dependent Association of SN-38 with Lipid Bilayers of a Novel Liposomal Formulation, International Journal of Pharmaceutics 299 (2005) 92-99.

* cited by examiner

SN-38 LIPID COMPLEXES AND THEIR METHODS OF USE

BACKGROUND OF THE INVENTION

This invention pertains to complexes of SN-38 with lipids, their methods of manufacture, and their use in the treatment of diseases, especially diseases involving eukaryotic cellular proliferation.

DESCRIPTION OF THE BACKGROUND

The compound known as 7-ethyl-10-hydroxycamptothecin (SN-38) and more formally as ((+)-(4S)-4,11-diethyl-4,9-dihydroxy-1H-pyrano[3',4':6,7]-indolizino[1,2-b]quinoline-3,14(4H,12H)-dione, first disclosed in U.S. Pat. No. 4,473,692, is an active metabolite of irinotecan, a derivative of camptothecin. It is thought to bind to the enzyme topoisomerase I, the enzyme responsible for relieving torsional strain in DNA by inducing reversible single-strand breaks. The bound SN-38 appears to block religation of the single-strand breaks by topoisomerase-I thereby causing cytotoxicity in mammalian cells which, apparently, can not otherwise sufficiently repair the breaks.

The metabolic conversion of irinotecan to SN-38 occurs primarily in the liver by carboxylesterase-mediated cleavage of the carbamate bond between the camptothecin moiety and a dipiperidino side chain. Subsequently, this derivative undergoes conjugation to form the glucuronide metabolite.

SN-38 is approximately 1000 times more potent than irinotecan as an inhibitor of topoisomerase I purified from human and rodent tumor cell lines. In vitro cytoxicity assays show that SN-38 is up to 2,000-fold more potent than irinotecan. Consequently, SN-38 has the potential to be a highly effective antineoplastic agent. In addition, SN-38 has an advantage over its camptothecin precursors in that it does not require activation by the liver. Therefore, an appropriate formulation could be used in local as well as systemic treatment methods.

SN-38 is exceedingly insoluble in aqueous solutions. Despite its lack of solubility in water, it also has a low affinity for lipid membranes from which it tends to precipitate into aqueous phase. These solubility characteristics interfere with the use of SN-38 as a therapeutic. Moreover, the effectiveness of SN-38 after repeated administrations can be limited by the development of multi-drug resistance which not only reduces its effectiveness but also reduces the effectiveness of certain other antineoplastic therapeutics. The general toxicity of SN-38 also limits its use therapeutically.

Thus, formulations are needed that improve SN-38 efficacy such that SN-38 can be used effectively in the treatment of diseases associated with cellular proliferation. Such a formulation should have suitable solubility and toxicity characteristics and will be useful in the treatment of certain proliferative diseases such as cancer.

The invention provides such a composition and methods. These and other advantages of the present invention, as well as additional inventive features, will be apparent from the description of the invention provided herein.

SUMMARY OF THE INVENTION

The present invention is for novel SN-38 compositions, their preparation methods, and their use in treating diseases caused by proliferating eukaryotic cells, such as cancer, particularly in mammals, especially humans. The SN-38 compositions include SN-38 complexed with a lipid wherein more than 50 wt. % of the SN-38 is complexed with the lipid. The complexes, include liposomes, and can contain any of a variety of neutral or charged lipid materials and, desirably, cardiolipin. Suitable lipids include any pharmaceutically acceptable lipophilic materials that bind SN-38 to provide a stable pharmaceutical formulation and facilitate its administration to mammals. Cardiolipin can be synthetic or derived from natural sources. The lipid complexes can carry net negative, or positive charges, or can be neutral. Preferred complexes also contain α-tocopherol. The SN-38 complexes can be used advantageously with secondary therapeutic agents other than SN-38, including antineoplastic, antifungal, antibiotic, or other active agents. Liposome complexes can be multilamellar vesicles, unilamellar vesicles, or their mixtures, as desired. The invention also encompasses methods for preparing such SN-38 complexes. The invention is further directed to methods in which a therapeutically effective amount of the SN-38 complexes are included in a pharmaceutically acceptable excipient and administered to a mammal, such as a human, to treat proliferative diseases, such as cancer.

In one particularly preferred method of preparing the SN-38 complexes. SN-38 is dissolved in an alkaline solution and used to hydrate a lipid film to form liposomes.

DETAILED DESCRIPTION OF THE PREFERRED EMBODIMENTS

The present invention provides compositions and methods for delivering SN-38 to a mammalian host. The compositions and methods are characterized by avoidance of solubility problems of SN-38, high SN-38 and complex stability, ability to administer SN-38 as a bolus or short infusion in a high concentration, reduced SN-38 toxicity, increased therapeutic efficacy of SN-38, and modulation of multidrug resistance.

The inventive composition is a lipid complex with SN-38 in which the complex desirably contains cardiolipin. Suitable complexes are characterized by having SN-38 bound with a lipophilic compound that imparts solubility characteristics such that stable pharmaceutical preparations can be generated and used. The complexes include, but are not limited to, liposomes and micelles. In the complexes the SN-38 can be bound to the lipid by covalent, hydrophobic, electrostatic, hydrogen, or other bonds and is considered bound even where the SN-38 is simply be entrapped within the interior of a liposome. The SN-38 compositions include SN-38 complexed with a lipid wherein about 50 wt. % or more of the SN-38 is complexed with the lipid, more preferably about 70 wt. % or more, even more preferably about 80 wt. % or more, and most preferably about 90 wt. % or more of the SN-38 is complexed with lipid.

Desirably, the SN-38 lipid complexes contain cardiolipin. Any suitable cardiolipin can be used. For example, cardiolipin can be purified from natural sources or can be chemically synthesized, such as tetramyristylcardiolipin, by such methods as are known in the art.

SN-38 complexes generally contain other complexing agents in addition to cardiolipin. Suitable agents include pharmaceutically acceptable synthetic, semi-synthetic (modified natural) or naturally occurring compounds having a hydrophilic region and a hydrophobic region. Such compounds include amphiphilic molecules which can have net positive, negative, or neutral charges or which are devoid of charge. Suitable complexing agents include compounds, such as phospholipids which can be synthetic or derived from natural sources, such as egg or soy. Suitable phospholipids include compounds such as phosphatidylcholine (PC), phosphatidylethanolamine. (PE), phosphatidylserine (PS), phosphatidylglycerol (PG), phosphatidic acid (PA), phosphatidylinositol (PI), sphingomyelin (SPM), and the like, alone or in combination. The phospholipids dimystoylphosphatidylcholine (DMPC), dimyristoylphosphatidylglycerol (DMPG), dioleoylphosphatidylglycerol (DOPG), distearoylphosphatidyl choline (DSPC), dioleoylphosphatidylcholine (DOPC), dipalmitoylphosphatidylcholine (DPPC), diarachidonoyl phosphatidylcholine (DAPC), or hydrogenated soy phosphatidylcholine (HSPC) can be used.

The SN-38 lipid complexes generally include at least one steroid component such as cholesterol, polyethylene glycol derivatives of cholesterol (PEG-cholesterols), coprostanol, cholestanol, or cholestane, or α-tocopherol. They may also contain sterol derivatives such as cholesterol hemisuccinate (CHS), cholesterol sulfate, and the like. Organic acid derivatives of tocopherols, such as α-tocopherol hemisuccinate (THS), can also be used. Suitable SN-38 complexes can also be formed with glycolipids, or natural or derivatized fatty acids and the like. The preferred SN-38 complexing agents include cardiolipin, a phosphatidyl choline, cholesterol, and α-tocopherol which are combined to form of a liposome.

Any suitable amount of SN-38 can be used. Suitable amounts of SN-38 are those amounts that can be stably incorporated into the complexes of the present invention. The SN-38 should preferably be present in the abovementioned compositions at a concentration of about 0.01 to about 5 mg/ml, more preferably about 0.1 to about 4 mg/ml, still more preferably about 0.5 to 3 mg/ml, and even more preferably about 0.8 to 2, or most preferably about 1 to 1.5 mg/ml SN-38.

Suitable compositions also generally contain from about 1 to about 50 wt. % cardiolipin, or preferably about 2 to about 25 wt. % cardiolipin, or more preferably about 5 wt. % to about 20 wt. % cardiolipin. Such compositions also generally contain about 1 wt. % to about 95 wt. % phosphatidylcholine, or more preferably about 20 wt. % to about 75 wt. % phosphatidylcholine. The preferred compositions also generally contain α-tocopherol in a concentration of about 0.001 wt. % to about 5 wt. %.

The complexing agents can also be considered liposome-forming materials when they are used to generate liposomes by methods such as are known. To generate the desired complexes, they can be dissolved by themselves or with the other lipophilic ingredients, including SN-38, in suitable solvents. Suitable solvents are those which provide sufficient solubility and can be evaporated without leaving a pharmaceutically unacceptable amount of a pharmaceutically unacceptable residue. For example, the cardiolipin can be dissolved in non-polar or slightly polar solvent such as ethanol, methanol, chloroform, or acetone. SN-38 can be dissolved in a non-polar, a slightly polar, or a polar solvent. Examples of suitable SN-38 solvents include methanol, chloroform, acetone, or aqueous alkaline solvent.

Generally, the method involves mixing dissolved lipophilic ingredients together and evaporating or lyophilizing the solvent(s) to form a homogeneous lipid film. Solvent evaporation can be by any suitable means that preserves the stability of the components. SN-38 can be said to be stable as long as most of the drug retains its chemical structure or a chemical structure that is in equilibrium with its chemical structure. Chemical structures in equilibrium with SN-38 specifically include structures that impart greater solubility at high pH but which are converted to SN-38 when the pH is lowered.

SN-38 complexes, including liposomes or micelles, can then be formed by adding a suitable solvent to the dry lipid film mixture. Suitable solvents include pharmaceutically acceptable polar solvents. Generally, solvents are aqueous solutions containing pharmaceutically acceptable salts, buffers, or their mixtures. In one method, a lipid film is hydrated with an aqueous solution of SN-38 having an alkaline pH. Suitable pHs range from about 7 to about 11, pHs of about 8 to about 10 are more preferred, and pHs of about 9 to about 10 are most preferred. Aqueous solutions having a suitable pH can be prepared from water having an appropriate amount of NaOH dissolved therein. Alternatively, such solutions can be prepared with buffers, such as Tris HCl, which have pKs within about 1 pH unit of the desired pH.

The liposome complexes are formed by dispersing the lipid in the aqueous solution with vigorous mixing. Any method of mixing can be used provided that the chosen method induces sufficient shearing forces between the lipid film and polar solvent to strongly homogenize the mixture and form the desired complexes. For example, mixing can be by vortexing, magnetic stirring, and/or sonicating. Where multilamellar liposomes are desired, they can be formed simply by vortexing the solution. Where unilamellar liposomes are desired, a sonication or filtration step is included in the process.

Liposomal SN-38 complexes can be prepared by mixing SN-38, cardiolipin, cholesterol, phosphatidyl choline and α-tocopherol in a suitable solvent to form a homogeneous mixture. The mixture is dried to form a lipid film and hydrated into liposomes by the addition of water or an aqueous solution and mixing.

Alternatively, SN-38 liposomes can be prepared by dissolving the lipophilic ingredients (with the exception of SN-38) together and evaporating them to form a lipid film. A solution of SN-38 is prepared in an aqueous solution at alkaline pH and used to hydrate the dry lipid film and form liposomes.

In general, any suitable method of forming liposomes can be used so long as it generates liposome entrapped SN-38. Multilamellar vesicles, stable plurilamellar vesicles, and reverse phase evaporation vesicles can be used. As can be appreciated, the present invention is intended to cover SN-38-entrapped liposome compositions, however made.

Suitable liposomes can be neutral, negatively, or positively charged, the charge being a function of the charge of the liposome components and pH of the liposome solution. For example, at neutral pH, positively charged liposomes can be formed from a mixture of phosphatidyl choline, cholesterol and stearyl amine. Negatively charged liposomes can be formed, for example, from phosphatidyl choline, cholesterol, and phosphatidyl serine.

Targeting agents can be bound to the SN-38 complexes such that the complexes can be targeted to particular tissues or organs. The agents can be bound through covalent, electrostatic, or hydrophobic bonds with the complexes. Suitable targeting agents include carbohydrates and proteins or other agents as are known to target desired tissues or organs. For example, U.S. Pat. No. 6,056,973, which is herein incorporated by reference, discloses a number of targeting agents and target cells. (See col. 11, 1. 1-41). Methods of preparing suitable conjugates are also disclosed. (See Col. 11, 1 55-col. 14, 1. 20).

SN-38 complexes can be filtered through suitable filters to control their size distribution. Suitable filters include those that can be used to obtain the desired size range of liposomes from a filtrate. For example, the liposomes can be formed and thereafter filtered through a 5 micron filter to obtain liposomes having a diameter of about 5 microns or less. Alternatively, 1 µm, 500 nm, 200 nm, 100 nm or other filters can be used to obtain liposomes having diameters of about 1 µm, 500 nm, 200 nm, 100 nm or any suitable size range, respectively. Alternatively, filtration can occur after formulation in liquid excipients or diluents, as hereinafter described.

When desired, liposomes can be dried such as by evaporation or lyophilization and the liposomes resuspended in any desirable polar solvent. Where liposomes are lyophilized, nonreducing sugars can be added prior to lyophilization to provide stability. One such suitable sugar is sucrose. Where liposomes are formed by hydrating lipid films with alkaline, aqueous solvents containing SN-38, it is desirable to use a low pH buffer to resuspend the lyophilized liposomes. Suitable solvents for resuspending the liposomes include for example a lactate buffered solution having a pH of about 3.5.

The invention includes pharmaceutical preparations which, in addition to non-toxic, inert pharmaceutically suitable excipients, contain the SN-38 complex and methods for preparing such compositions. By non-toxic, inert pharmaceutically suitable excipients there are to be understood solid, semi-solid or liquid diluents, fillers and formulation auxiliaries of all kinds.

The invention also includes pharmaceutical preparations in dosage units. This means that the preparations are in the form of individual parts, for example capsules, pills, suppositories and ampoules, of which the content of the SN-38 complex corresponds to a fraction or a multiple of an individual dose. The dosage units can contain, for example, 1, 2, 3 or 4 individual doses or ½, ⅓ or ¼ of an indiv dose. An individual dose preferably contains the amount of SN-38 which is given in one administration and which usually corresponds to a whole, a half, a third, or a quarter of a daily dose.

Tablets, dragees, capsules, pills, granules, suppositories, solutions, suspensions and emulsions, pastes, ointments, gels, creams, lotions, powders and sprays can be suitable pharmaceutical preparations.

For the oral mode of administration, the SN-38 complex can be used in the form of tablets, capsules, losenges, powders, syrups, aqueous solutions, suspensions, and the like. Carriers such as lactose, sodium citrate, and salts of phosphoric acid can be used to prepare tablets. Further, disintegrants such as starch, and lubricating agents, such as magnesium stearate, sodium lauryl sulfate and talc can be included. Diluents such as lactose and high molecular weight polyethylene glycols can be used in the preparation of dosages in capsule form. The active ingredient can be combined with emulsifying and suspending agents to generate aqueous suspensions for oral use. Flavoring agents such as sweeteners can be added, as desired.

For topical administration and suppositories drug complexes can be provided in the form of such gels, oils, and emulsions as are known by the addition of suitable water-soluble or water-insoluble excipients, for example polyethylene glycols, certain fats, and esters or mixtures of these substances. Suitable excipients are those in which the drug complexes are sufficiently stable to allow for therapeutic use.

The abovementioned pharmaceutical compositions are prepared for administration in the usual manner according to known methods, for example by mixing the complexed SN-38 with suitable excipient(s).

The present invention also includes the use of SN-38 according to the invention and of pharmaceutical preparations which contain SN-38 according to the invention in human and veterinary medicine for the prevention, amelioration and/or cure of diseases, in particular those diseases caused by cellular proliferation, such as cancer, in any mammal, such as a cow, horse, pig, dog or cat. However, it is particularly preferred for use in the treatment of human patients, particularly for cancer and other diseases caused by cellular proliferation. The inventive compositions have particular use in treating human lymphoma, ovarian, breast, lung and colon cancers in addition to multiple sclerosis.

The active compound or its pharmaceutical preparations can be administered orally, parenterally, intraperitoneally, rectally, or by intratumoral injection. As SN-38 does not require activation by the liver, it is advantageous to employ the present compositions locally, such as by directed injection into an arm or leg, or in the case of a human, a hand.

In a human of about 70 kg body weight, for example, about 0.1 to 2 mg or about 0.5 to 1 mg SN-38 can be administered per kg of body weight can be administered. Preferably, about 0.5 to 2.0 mg of SN-38 per kg of body weight is administered. However, it can be necessary to deviate from the dosages mentioned and in particular to do so as a function of the nature and body weight of the subject to be treated, the nature and the severity of the illness, the nature of the preparation and if the administration of the medicine, and the time or interval over which the administration takes place. Thus it can suffice in some cases to manage with less that the abovementioned amount of active compound whilst in other cases the abovementioned amount of active compound must be exceeded. The particular required optimum dosage and the type of administration of the SN-38 can be determined by one skilled in the art, by available methods. Suitable amounts are therapeutically effective amounts that do not have excessive toxicity, as determined in empirical studies.

A significant advantage of cardiolipin-containing compositions is that they provide a method of modulating multidrug resistance in cancer cells which are subjected to SN-38. In particular, the present compositions reduce the tendency of cancer cells subjected to chemotherapy with SN-38 to develop resistance thereto, and reduces the tendency of cancer cells to develop resistance to other therapeutic agents, such as taxol or doxorubicin. Thus, other agents can be advantageously employed with the present treatment in combination with SN-38.

Having described the present invention, reference will now be made to certain examples which are provided solely for purposes of illustration and which are not intended to be limiting.

EXAMPLE 1

SN-38 (3 μmoles) can be dissolved in chloroform containing 3 μmoles cardiolipin. To this mixture, 14 μmoles of phosphatidyl choline dissolved in hexane and 10 μmoles cholesterol in chloroform can be added. The mixture can be stirred gently and the solvents can be evaporated under vacuum at below 30° C. to form a thin dry film of lipid and drug. Liposomes can then be formed by adding 2.5 ml of saline solution and aggressively mixing the components by vortexing. The flasks can then be vortexed to provide multilamellar liposomes and optionally sonicated in a sonicator to provide small unilamellar liposomes. The efficiency of SN-38 encapsulation can be determined by dialyzing an aliquot of the subject liposomes overnight in a suitable aqueous solvent or centrifuging an aliquot of the subject liposomes at 50,000×g. for 1 hour. Thereafter the liposome fraction is dissolved in methanol and analyzed by standard methods using high pressure liquid chromatography (HPLC), such as reverse phase HPLC. Generally the encapsulation efficiency of SN-38 in liposomes will be between 80 to 95% of the initial input dose.

EXAMPLE 2

Similar experimental conditions can be utilized with varying quantities of drug and lipid. For example, concentrations of 6 μM SN-38, 6 μM cardiolipin, 28 μM phosphatidyl choline and 20 μM cholesterol can be used by dissolving them in a suitable solvent, evaporating the solvent, and dispersing the dried lipid/drug film in a suitable aqueous solvent such as 5 ml of 7% trehalose-saline solution. Hydration of the liposomes can be facilitated by vortexing and/or sonicating the mixture. The liposomes can then be dialyzed, as desired, and the percent encapsulation of SN-38 in liposomes measured, as described above. Typically, SN-38 encapsulation will be greater than about 75% and more generally between about 85 to 95% or more as assayed by HPLC.

EXAMPLE 3

SN-38 can be encapsulated in liposomes by using 3 µM of the drug, 15 µM of dipalmitoyl phosphatidyl choline, 1 µM cardiolipin, and 9 µM cholesterol in a volume of 2.5 ml. The drug and lipid mixture can be evaporated under vacuum and resuspended in an equal volume of saline solution. The remainder of the process can be similar to that described above. The SN-38 encapsulation efficiency will generally be higher than 75% in this system.

EXAMPLE 4

In this example, liposomes containing 2 µM SN-38, 2 µM of phosphatidyl serine, 11 µM phosphatidyl choline, 2 µM cardiolipin, and 7 µM cholesterol prepared by the method described in Example 1 is contemplated with greater than 75% SN-38 encapsulation efficiency.

EXAMPLE 5

In this example liposomes containing over 1 mg/ml SN-38 in solution are demonstrated.

A lipid film is prepared by adding about 0.2 g of D-α-tocopherol acid succinate to about 1 kg of t-butyl alcohol which is warmed to about 35-40° C. The solution is mixed for about 5 min until the tocopherol is dissolved. About 6.0 g of tetramyristoyl cardiolipin is added to the solution and the solution is mixed for about 5 minutes. About 10 g of cholesterol is added to the solution and the solution is mixed for about 5 more minutes then about 30 g of egg phosphatidyl choline is added and mixed for another 5 min. Approximately 11 grams of the resulting lipid solution is lyophilized to generate a lipid film.

To prepare liposomal SN-38, a 1.2 mg/ml solution of SN-38 is prepared by dissolving the drug in an aqueous alkaline solution having a pH of between 8 and 10. Approximately 15 ml of this SN-38 solution is added to a vial containing the lipid film. The vial is swirled gently, allowed to hydrate at room temperature for 30 min, vortexed vigorously for 2 min, and sonicated for 10 min in a bath-type sonicator at maximum intensity. The pH of the liposome solution is reduced to acid pH. Using this method more than 90 wt. % of the SN-38 is complexed with lipid in the form of liposomes.

Having described the present invention it will be apparent that one skilled in the art can make many changes and modifications to the above-described embodiments without departing from the spirit and scope of the present invention.

The following document is hereby incorporated by reference: published international patent application WO 02/058622.

What is claimed is:

1. A method of forming a lipid composition comprising SN-38 and liposomes, said method comprising:
   forming a lipid phase comprising cardiolipin;
   hydrating the lipid phase with an aqueous solution of SN-38 having an alkaline pH so as to form said lipid composition with about 70 wt. % or more of non-precipitated SN-38 entrapped in the liposomes; and
   reducing the pH of the lipid phase to an acidic pH.

2. The method of claim 1, further comprising adding a nonreducing sugar to the lipid composition, wherein the lipid phase is formed in an organic solvent, and said hydrating the lipid phase is carried out after removing the organic solvent.

3. The method of claim 1, wherein the lipid phase comprises at least one lipid selected from the group consisting of phosphatidylcholine, phosphatidylethanolamine, phosphatidylserine, phosphatidylglycerol, phosphatidic acid, phosphatidylinositol, sphingomyelin, sterol, tocopherol, fatty acid, and mixture thereof.

4. The method of claim 1, wherein the lipid phase further comprises a phosphatidylcholine, a sterol and a tocopherol.

5. The method of claim 1, wherein the lipid phase further comprises a phosphatidylglycerol selected from the group consisting of dimyristoylphosphatidylglycerol, dioleoylphosphatidylglycerol, distearoylphosphatidylglycerol, dipalmitoylphosphatidylglycerol, diarachidonoylphosphatidylglycerol, or mixture thereof.

6. The method of claim 1, wherein the lipid phase further comprises a phosphatidylcholine selected from the group consisting of dimyristoylphosphatidylcholine, distearoylphosphatidylcholine, dioleoylphosphatidylcholine, dipalmitoylphosphatidylcholine, diarachidonoylphosphatidylcholine, egg phosphatidylcholine, soy phosphatidylcholine, hydrogenated soy phosphate, dylcholine, and mixture thereof.

7. The method of claim 1, wherein the lipid phase further comprises a sterol selected from the group consisting of cholesterol, polyethylene glycol derivatives of cholesterol, coprostanol, cholestane, cholesterol hemisuccinate, cholesterol sulfate, and mixtures thereof.

8. A lipid composition comprising SN-38 prepared in accordance with the method of claim 1.

9. The method of claim 1, wherein the lipid phase further comprises cholesterol, a tocopherol, and dioleoylphosphatidylcholine, and wherein the lipid phase is formed in ethanol.

10. A liposomal composition prepared according to the method of claim 4.

11. A liposomal composition prepared according to the method of claim 5.

12. A liposomal composition prepared according to the method of claim 6.

13. A liposomal composition prepared according to the method of claim 7.

14. A liposomal composition prepared according to the method of claim 1, wherein the concentration of SN-38 in the composition is between about 0.1 mg/ml and about 2.0 mg/ml.

* * * * *